United States Patent [19]

Wakabayashi

[11] Patent Number: 5,176,649
[45] Date of Patent: Jan. 5, 1993

[54] INSERTION DEVICE FOR USE WITH CURVED, RIGID ENDOSCOPIC INSTRUMENTS AND THE LIKE

[76] Inventor: Akio Wakabayashi, 2617 E. Chapman Ave., Orange, Calif. 92667

[21] Appl. No.: 646,175

[22] Filed: Jan. 28, 1991

[51] Int. Cl.⁵ .......................................... A61M 31/00
[52] U.S. Cl. ..................................... 604/164; 604/264
[58] Field of Search ............... 604/164, 264, 280, 275, 604/180

[56] References Cited

U.S. PATENT DOCUMENTS

| | | | |
|---|---|---|---|
| 4,790,831 | 12/1988 | Skribiski | 604/280 |
| 4,978,334 | 12/1990 | Toye et al. | 604/164 |
| 4,994,027 | 2/1991 | Farrell | 604/164 |
| 5,057,083 | 10/1991 | Gellman | 604/280 |

Primary Examiner—Paul J. Hirsch
Attorney, Agent, or Firm—Willie Krawitz

[57] ABSTRACT

A flexible insertion device is provided for inserting an endoscope or endoscopic operating instrument through the body wall, typically the chest or abdominal wall. The insertion device comprises a collapsible rigid plastic or metal trocar inserter and a surrounding thin, plastic sheath with an adhesive collar. The insertion device enables the maintaining of air-tight sealing and permits the insertion of rigid, curved instruments without becoming dislodged from the body wall musculature. This eliminates the necessity of multiple puncture and insertion procedures which otherwise would cause additional tissue injuries.

6 Claims, 1 Drawing Sheet

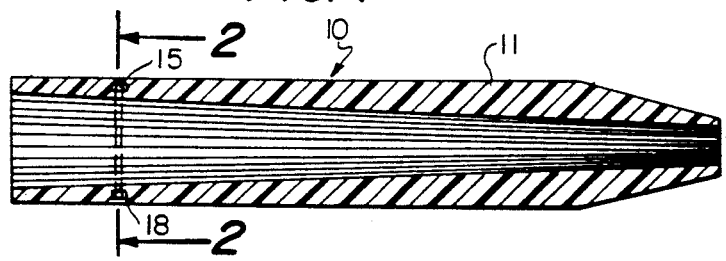
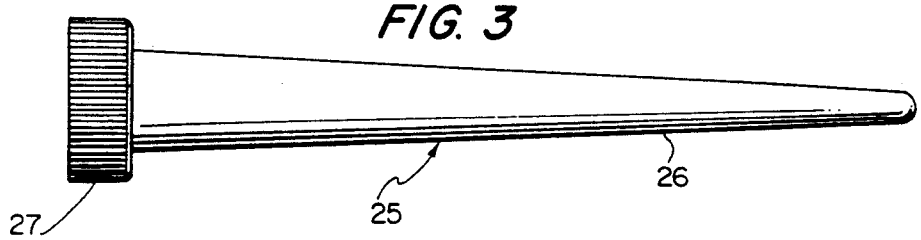
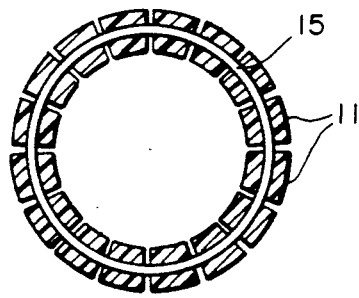
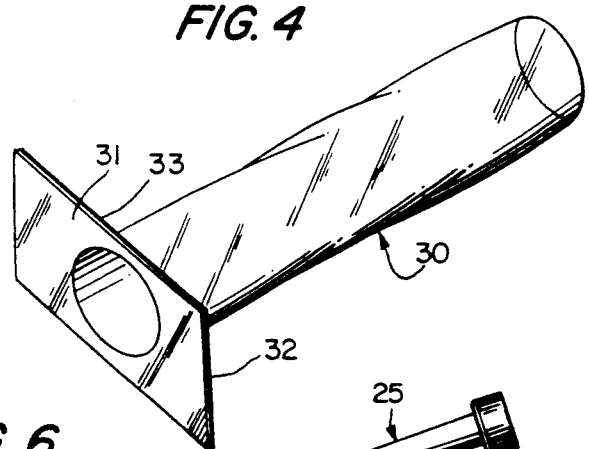
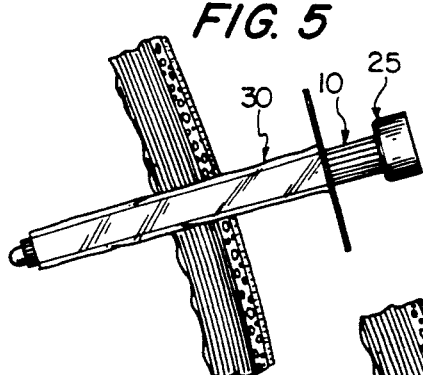
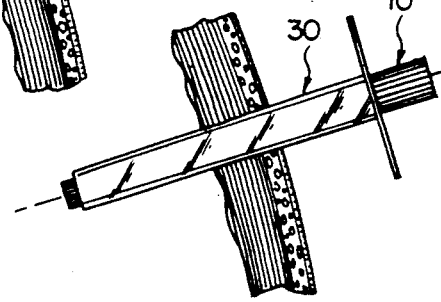
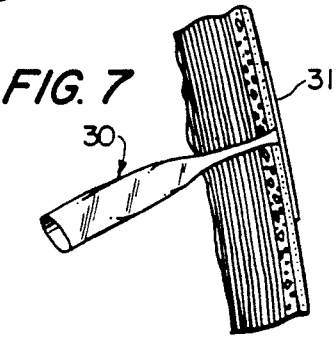

INSERTION DEVICE FOR USE WITH CURVED, RIGID ENDOSCOPIC INSTRUMENTS AND THE LIKE

BACKGROUND OF THE INVENTION

This invention relates to a new and improved insertion assembly for facilitating the insertion of curved endoscopic instruments into a body cavity, typically the pleural or peritoneal space of a patient.

Conventional trocars are made in the form of a tube, and include an obturator, which are manufactured from a rigid metal or plastic tube. Following withdrawal of the obturator, the trocar will remain in place in the body wall. Due to the rigidity of these conventional trocars, the passage of any curved instruments therethrough is prevented, and also a one-way valve is required if air-tight sealing is needed during a laparoscopy.

Consequently, there is desired an insertion device which enables the insertion of curved, rigid endoscopic operating instruments therethrough.

Also, an insertion device is desired which can be securely fastened to the body wall, and hence which will minimize the necessity of requiring multiple punctures and insertions with consequent injury to tissues.

THE INVENTION

According to the invention, an assembly of a rigid, collapsible insertion device and a flexible, collapsible plastic sheath with an adhesive collar is provided. The insertion device comprises two parts, one part being a core pin, and the other part being a collapsible obturator comprising a plurality of ribs which are loosely bound together with a ring piercing through the eyes of the ribs.

The insertion device components are inserted into the patient's body cavity through a body wall, typically the chest or abdominal wall. Once the device has been completely inserted, the core pin is withdrawn, causing the obturator to collapse, which facilitates its withdrawal from the sheath. Following withdrawal of the trocar, the sheath is secured in the body wall by its adhesive collar, and this enables the multiple passage of an endoscope or an endoscopic operating instrument during the endoscopic procedure.

As the endoscope or endoscopic operating instrument is inserted through the plastic sheath, the tension of the abdominal wall muscles compresses the surrounding sheath and causing it to seal the intraperitoneal air, thereby maintaining the desired pneumoperitoneum, although this feature is not necessary for a thoracoscopy. Following termination of the endoscopic procedure, the instruments and plastic sheath are withdrawn.

BRIEF DESCRIPTION OF THE DRAWINGS

FIG. 1 is a cross sectional view in longitudinal section showing the collapsible obturator device;

FIG. 2 is a cross sectional end view taken along the lines 2—2 of FIG. 1;

FIG. 3 is a longitudinal side elevation view of the insertion pin for the obturator;

FIG. 4 is an external, perspective view showing the plastic sheath employed for use with the obturator;

FIG. 5 is a view in sectional side elevation showing the sheath pin and trocar being inserted into a patient;

FIG. 6 is a view in sectional side elevation showing withdrawal of the pin from the obturator; and, FIG. 7 is a view in sectional side elevation of the collapsible sheath after the collapsed obturator is withdrawn.

DESCRIPTION OF THE PREFERRED EMBODIMENTS

The rigid, collapsible obturator 10 of this invention is shown in FIG. 1, and comprises a plurality of longitudinal solid ribs 11 which are typically constructed of a medical grade 304 stainless steel or rigid plastic. These ribs 11 are loosely secured at their proximal ends 13 by a retention ring 15 shown in FIG. 2. An eye element 18 formed near the end of each rib 11, and ring 15 passes through the eye element to secure the ribs of the obturator together. A pin element 25 shown in FIG. 3, comprises a pin 26 and attached handle 27, the pin being insertable into the collapsible obturator 10.

A collapsible sheath 30 is shown in FIG. 4, comprises a plastic material such as polyethylene, polypropylene, teflon, 5 etc., having a collar portion 31 with a skin securing adhesive material 32 coating the underside 33 of the collar. When assembled (FIG. 5), the pin 26 is inserted into the obturator 10 and outwardly compresses the longitudinal solid ribs 11 against the plastic sheath. The assembled device of FIG. 5 is shown being inserted into the patient through a body wall.

When pin element 25 is withdrawn, as shown in FIG. 6, the collapsible ribs 11 of the obturator 10 will collapse inside the sheath. Consequently, the obturator can be easily removed from the plastic sheath, as shown in FIG. 7, and the sheath remains in place without being totally collapsed or obstructed by the body wall. Subsequently, insertion of curved, rigid endoscopic instruments can be made into the body cavity of a patient. If the gap between the endoscopic instrument and the sheath is sufficiently small, then the musculature of the body wall will seal off the gap, and air leakage of the pneumoperitoneum will not occur. However, if the endoscopic instrument is too small, a sufficiently large gap between the endoscope and sheath will be formed; consequently, a plug or elastic insert (not shown) would be required to prevent air leakage.

The assembly and method of this invention is inexpensive and simple, and enables a surgeon to readily examine a patient while reducing the trauma associated with such a procedure.

I claim:

1. An insertion device for curved, rigid endoscope or endoscopic instruments, and the like, comprising:
   a.) a collapsible obturator comprising a plurality of loosely connected ribs;
   b.) a pin element adapted for insertion into one end of the obturator; and,
   c.) a collapsible sheath surrounding the obturator; whereby,
      i. the obturator is compressed outwardly when the pin element is inserted therein, thereby causing the obturator to contact the sheath and form an assembled device adapted for insertion through a body wall of a patient, the sheath being secured to the patient's body wall;
      ii. removal of the pin element from the obturator will cause the obturator to collapse inside the sheath and enable its withdrawal form the sheath and the patient, leaving the sheath in place in the patient without being completely collapsed or obstructed by the body wall, thus facilitating multiple insertions and withdrawals therethrough of a rigid, curved endoscope or endoscopic instrument, without air leakage; and, iii. following an endoscope procedure, the sheath can be withdrawn from the patient.

2. The insertion device of claim 1, in which the said ribs of the obturator are connected by a retention ring.

3. The insertion device of claim 1, in which the sheath is adhesively secured to the body wall of the patient.

4. The insertion device of claim 3, in which the sheath provides a collar defining an underside having an adhesive coating, and the sheath is secured to the body wall of the patient by means of the said adhesive.

5. The insertion device of claim 1, in which the sheath is constructed of materials selected from the class consisting of polyethylene, teflon and polypropylene.

6. The insertion device of claim 2, in which the ribs of the said collapsible obturator define eye elements, and the retention ring passes through the eye elements to secure the ribs of the obturator together.

* * * * *